(12) United States Patent
Kenway

(10) Patent No.: US 6,346,704 B2
(45) Date of Patent: *Feb. 12, 2002

(54) DEFECT DETECTION IN ARTICLES USING COMPUTER MODELLED DISSIPATION CORRECTION DIFFERENTIAL TIME DELAYED FAR IR SCANNING

(75) Inventor: Daniel J. Kenway, Edmonton (CA)

(73) Assignee: OSB Scan Inc., Edmonton (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/097,392

(22) Filed: Jun. 16, 1998

Related U.S. Application Data

(63) Continuation-in-part of application No. 09/092,035, filed on Jun. 5, 1998.
(60) Provisional application No. 60/048,828, filed on Jun. 6, 1997.

(51) Int. Cl.[7] .................................................. G01N 25/72
(52) U.S. Cl. .................... 250/341.6; 250/330; 250/358.1
(58) Field of Search ................................ 250/330, 340, 250/341.1, 341.6, 358.1, 359.1, 362

(56) References Cited

U.S. PATENT DOCUMENTS

| 4,866,276 A | * | 9/1989 | Leavens et al. ............. 250/341 |
| 5,631,465 A | * | 5/1997 | Shepard ....................... 250/330 |
| 6,013,915 A | * | 1/2000 | Watkins ................... 250/341.1 |

* cited by examiner

*Primary Examiner*—Constantine Hannaher
*Assistant Examiner*—Albert Gagliardi
(74) *Attorney, Agent, or Firm*—Ridout & Maybee

(57) ABSTRACT

A process for the detection of flaws in an article comprising infra-red scanning of the article as its temperature changes and comparing the infra-red scans for regularity of cooling/heating pattern. Where the article is irregular, such as in marginal areas, thermodynamic modelling is performed to establish a hypothetic cooling/heating pattern for an unflawed article.

7 Claims, 10 Drawing Sheets

DEFLECT DETECTION BY COMPUTER MODELLED
DISSIPATION CORRECTION TIME DELAYED FAR IR
SCANNING

Infrared Measured Panel Temperature (Degrees Celsius)

DEFECT DETECTION IN ARTICLES USING COMPUTER MODELLED DISSIPATION CORRECTION DIFFERENTIAL TIME DELAYED FAR IR SCANNING

RELATED APPLICATIONS

This application is a continuation-in-part of application Ser. No. 09/092,035 filed Jun. 5, 1998 by Daniel J. Kenway claiming priority from U.S. Provisional Patent Application No. 60/048,828 filed Jun. 6, 1997.

BACKGROUND OF THE INVENTION

1. Field of the Invention

The invention relates to defect detection in articles using computer modelled dissipation correction differential time delay Far infra-red scanning. Especially the invention relates to such defect detection in articles such as fibre board panels, oriented strand board panels, medium density fibre board panels, metal panels, metal pipes, coated metal pipes and similar articles.

2. Acknowledgement of the Prior Art

Non-destructive testing inspection using Far IR scanning is well known in the detection of hot spots for example detecting where insulation is absent, where friction components are malfunctioning, or where cooling/exhaust systems are failing. However, flaws which do not cause local hot spots are more difficult to detect. Some of these flaws are very hard to detect.

Various attempts have been made to overcome the difficulties which arise in this type of scanning for flaws. Examples of methods which have been used are set out in U.S. Pat. No. 5,357,112 issued Oct. 18, 1994 to Steele et al., U.S. Pat. No. 5,444,241 issued Aug. 22, 1995 to Del Grande et al., and U.S. Pat. No. 5,631,465 issued May 20, 1997 to Shepard.

The horizontal density variation of Oriented Strand Board (OSB) affects most of the physical and mechanical properties of the panel. Between-panel density variation can well be measured and controlled. Within-panel variation, however, has been difficult to measure. A better estimation of this horizontal density variation obviously could provide information for controlling the mat forming process to reduce density variation. A more uniform density distribution would allow for a reduction in panel thickness or density, which would eventually improve wood fibre utilization.

Destructive measurements of OSB panel density are usually slow and expensive in terms of labor cost. There is a need for methods of nondestructive measurements of OSB density both at laboratory and industrial scales.

SUMMARY OF THE INVENTION

It has been observed qualitatively that variation in density could be detected using a Far infra-red imaging system. IR thermography technology was used to estimate OSB panel density.

The fact that radiation is a function of object surface temperature makes it possible for an IR camera to calculate and display this temperature. If an OSB panel contains an anomaly in its density, and the panel starts at an initial uniform temperature, then as it is quickly heated and cooled, the anomaly will produce an anomaly in the distribution of surface temperature. This is because, in the course of temperature change, those areas of the panel which have lower density will lose or gain heat more rapidly and high density areas lose or gain heat more slowly. This is the basic theoretical principle on which infrared OSB density measurement is based. An aim of this invention was to determine the accuracy, spatial resolution and speed of IR measurement of OSB panel density.

It has also been surprisingly discovered that in a large central area of an article it is not necessary to resort to various precautions to overcome difficulties. It is only necessary to utilize precautions in a marginal area where cooling of an unflawed article does not occur in such a set pattern as in a central area.

The present invention provides a process for the detection of flaws in an article, especially OSB, using Far infra-red scanning of its surface comprising changing the temperature of the surface of an article over a plurality of temperatures and making an infra-red scan at each of said temperatures during changing the temperature, the infra-red scans being separated one from another by equal time increments; characterized in the steps of allocating parts of said surface as central and marginal parts forming images from said infra-red scans, digitizing said infra-red scans, digitizing the images to provide a sequence of digitized scanned images; for said central part of the surface, comparing data directly from said digitized scanned images and noting variations and/or anisotropies from a general cooling pattern for the article and deducing the presence of flaws at locations in the article corresponding to the location of the variations and/or anisotropies in the comparison of the digitized scanned images; and for the marginal part of the surface, performing thermodynamic modelling on one of the digitized scanned images to provide an estimate of the temperature distribution for a hypothetic unflawed article after passage of one of said time increments, and comparing data from an adjacent digitized scanned image with said estimate and noting variations and/or anisotropies of the structure of the marginal part of the article.

The present invention also provides a process for detection of flaws in an article, especially in OSB. This process comprises changing the temperature of the surface of an article over a plurality of temperatures; making an infra-red scan at each of said temperatures during changing of temperature; said infra-red scans providing at least a first and a second scanned image and being separated one from the other by a time increment; digitizing the at least first and second scanned images to provide a sequence of at least a first and a second digitized scanned image; performing thermodynamic modelling on the first digitized scanned image to provide an estimate of the temperature distribution for a hypothetic unflawed article after passage of said time increment; comparing data from said second digitized image with said estimate, noting variations and/or anisotropies of the structure of the article. Thereafter, quality decisions about the fitness of the article can be made.

While first and second scans at first and second temperatures may be sufficient to provide data for flaw detection, a group of scans may be made at a series of three or more temperatures for greater accuracy. Said thermodynamic estimate may be made at any one of this series of temperatures and may be compared with data from scanned images obtained at higher or lower temperatures.

The relative proportion of the central and marginal parts may be chosen in accordance with the shape and size of the article, the material from which it is made and the degree of accuracy required. For example, if the article is a circular metal plate of say 10 feet in diameter, the central portion may be a 9 foot circle within an annular marginal portion. If the plate is formed of a less thermally conductive material, the marginal portion may be smaller. If, however, the plate is square, the central portion may possibly still be circular, since the corners of the square cause irregularities. Many of the decisions will be within the skill of the operator once the general principle is appreciated may be made by a man skilled in the art. In very general terms the central portion may be of regular shape and may be from 10–90% of the surface area of the article.

More particularly the central part may be from 20–80% or especially 75% of the surface area of the article.

The process of specifically inducing, or introducing a heating or cooling transient, with the specific intention of creating a temporary temperature differential in what would have otherwise been a steady state situation is particularly important. The creation of, high speed monitoring of, image acquisition of, image processing of, enhancement of, and thermodynamic modelling of, these temporary temperature differences constitutes the essence of this invention.

Conveniently the thermodynamic modelling and the comparison of data are performed by a suitably programmed computer.

In the following specific detailed discussion, it is always assumed that a surface of the article to be tested is heated above ambient temperature and allowed to cool. In fact, it is within the scope of the invention to cool the article below ambient temperature and allow it to heat up to obtain two incremental temperature differences.

While the following detailed discussion is limited to the scanning and comparison of only two images at different temperatures, it is clear that a much larger number of images may be scanned and compared.

For example, the process may comprise the following steps:
1. Central and marginal parts are designated if desired.
2. The component to be inspected is heated so that its temperature rises significantly above ambient temperature. This heating is preferably uniform, and preferably of at least 50 degrees Celsius in magnitude.
3. An IR image of the surface of the heated component to be analysed is obtained with sufficient resolution (in temperature, spatial, and temporal domains) to allow for detection of defects. The spatial resolution required will depend on the defects in question (for example variation in oriented strand board (OSB) panels might require resolution of ¼" square, variations in pipe wall thickness might require resolution of 0.5 mm square). The temperature resolution required from the Far IR image will typically be from 0.1 to 0.2 degrees Celsius. Typically the scanner will be a forward looking infra-red (FLIR) scanner using a cooled mercury cadmium telluride detector, or a cooled indium arsenide detector or even an uncooled micro-bolo metric array. The details of the scanner implementation are not important as long as:
   a) the resolution is adequate,
   b) the image acquisition speed is adequate (some thermal transients are of short duration)
   c) the image can be acquired in the appropriate setting (real time acquisition for in plant production monitoring, remote portable and field worthy acquisition for in-situ applications).
   d) the acquisition speed and mode is appropriate to the application (e.g. linear or flying spot scanning may be necessary for moving web processes, where as a real or snapshot acquisition may be necessary for quasi-stationary processes).
4. The scanned Far IR (3–10 micrometers wavelength of peak sensitivity) image is digitized and stored. The pixel resolution of the digitization and the storage system must be adequate to preserve the spatial resolution of the original IR data.
5. After a suitable time interval (this interval may vary from a fraction of a second in the case of a pipeline in use, to tens of minutes for large structures like the hulls of ships which have only been minimally heated), a second Far IR image of equivalent resolution is sampled and digitized. For the central part of the first and second images may be compared directly. For the marginal part thermodynamic modelling as described in the following steps may be used. If central and marginal parts are not designated then thermodynamic modelling is performed on the whole.
6. Standard thermodynamic modelling involving specific heats, conductivities, temperature differentials from ambient, and rough convection and other loss estimates is applied to the component data for the first sample, and the temperature distribution for a "perfect homogeneous" component at the instant of the second sampled is modelled and estimated. Alternately, this estimate may be derived from images of "good" articles taken at the second sampling time. The main purpose of calculating this estimate is to account for the significant non-uniformity of heat loss that arises directly from thermo-dynamics of the situation, so that comparison of the estimated temperature distribution with the actual will not high light any local anomalies.
7. The modelled radiant temperature profile estimate at the time of the second sampling is then compared with the actual profile data from the second sampling and the difference calculated, or high lighted.
8. Significant variation or anisotropies from within three dimensional structure then become evident. These may correspond to flaws or other non-uniformities.
9. The variations, and anisotropies evident in the image, can then be further enhanced using conventional image processing techniques, and:
   a) presented in the form of a visual spot
   b) quantified and used to make a pass/fail or grading decision.

It is believed the process of the invention is especially applicable to:
1. The inspection of pressed composite panel, such as OSB, or laminated products, in a production environment for anisotropies, resin spots and delaminations or other defects.
2. The in-situ inspection of structural panels on ships storage tanks, and other large structures; for external corrosion, paint or coating delamination, the buildup of layers or other defects.
3. The in-situ inspection of wall thickness variations in pipelines. In this case no marginal part is designated, or the marginal part involves only the ends of the pipes.

BRIEF DESCRIPTION OF THE DRAWINGS

Embodiments of the invention will now be described by way of example with reference to the drawings in which.

DETAILED DESCRIPTION OF THE PREFERRED EMBODIMENTS

Hot Pressed Composite Panel Inspection

Figure 1:
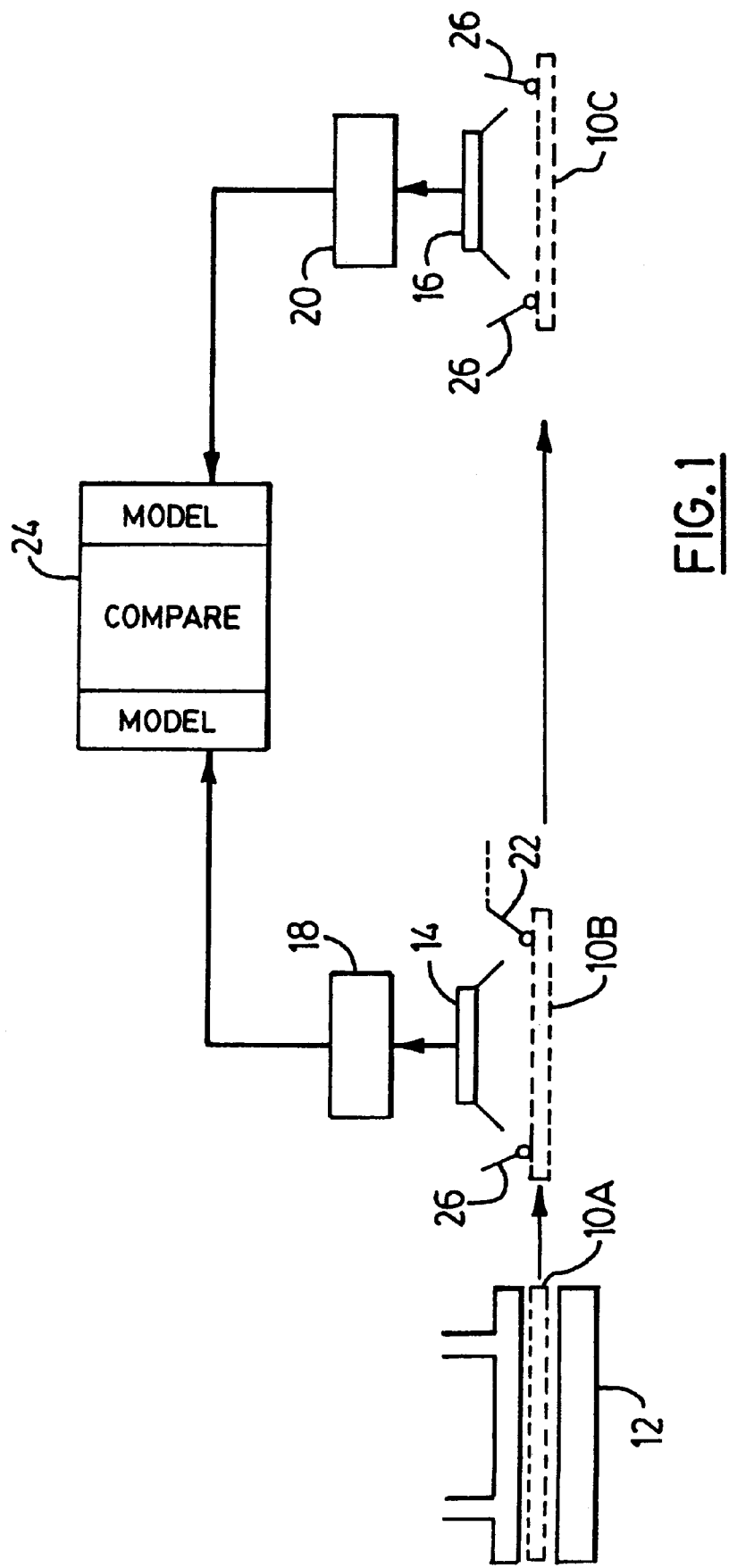
FIG. 1 is a schematic representation of one embodiment of the invention.

The production of oriented strand board (OSB), medium density fibre board (MDF), hot pressed laminated composites, and other pressed materials is a complex process. It is highly desirable to monitor process variability, e.g. to note variations in the placement of wood chips, fibre components, density, distribution of resin, local delamination, and other non-uniformities in the panel. Process variations from the mean intended usually result in a degradation of local properties (too brittle, too soft, too stiff, wrong colour, too weak, etc.).

Embodiments of the invention will now be described which allows for a direct on-line measurement of these production variations.

Since the panels undergo a hot pressing, they emerge from the press already uniformly heated. Therefore, apparatus used may be as follows:

1. A first Far IR scanner capable of imaging the moving OSB with the required resolution.
2. A digitization and storage unit that buffers and sequences the first images taken.
3. A second independent Far IR scanner identical or similar resolution to the first that images the panels at a latter point in their transport and processing in the facility.
4. Sufficient tachometers, broken beam sensors, and local ambient thermometers to allow for accurate and efficient tracking of the panels, and thermodynamic modelling of the associated heat loss in transport.
5. An image processing computer system capable of performing the thermodynamic modelling calculations of the set of first images and computing the differences between these time forward modelled first temperature distributions, and actual second temperature distribution sampled.
6. Image processing hardware and software capable of enhancing, identifying and quantifying the detected variations between the actual IR image samples, and the time forward modelled data from the earlier images.
7. A process control interface to the PLC or control equipment which controls the sorting, marking, and grading of the panel products being produced.

Panels are heated in a hot pressing step of their manufacture to high temperatures, e.g. 60 to 120 degrees Celsius above ambient. Panels are transported from the hot press typically at speeds of up to 400 ft. per minute. Temperature differences are large. In the ideal embodiment, the two IR scanners are placed as far apart as possible within a section of the production facility where motion of the panels is relatively uniform. The panels are scanned at different temperatures and the images are digitized.

A central portion and a marginal portion may be designated for each panel. This designation is dependent on the accuracy required in the marginal area but for general purposes the central area may comprise between about 10 and 90% of the surface area. Usually the central area may be about 75% of the surface. For the rectangular panel shown in FIG. 1A, the marginal part is advantageously increased at the corners since irregularities in cooling or heating may occur. Thus the central area may have smoothed corners as shown or may even be circular.

Spatial resolutions of on the order of ¼" square are required, and image processing systems must store and process 400×200 pixels/image for 8'×4' panels, and up to 1200×600 pixels/image for 24'×12' panels.

Thermodynamic modelling, for the marginal portion or when no central portion is designated, is calculated by means of a computer and the variations and anisotropies indicate flaws in the panels.

Adequate image and mathematical processing must be provided (several billion operation per second) to perform image processing and thermodynamic modelling at rates up to 1 panel every 0.5 second.

Figure 1A:
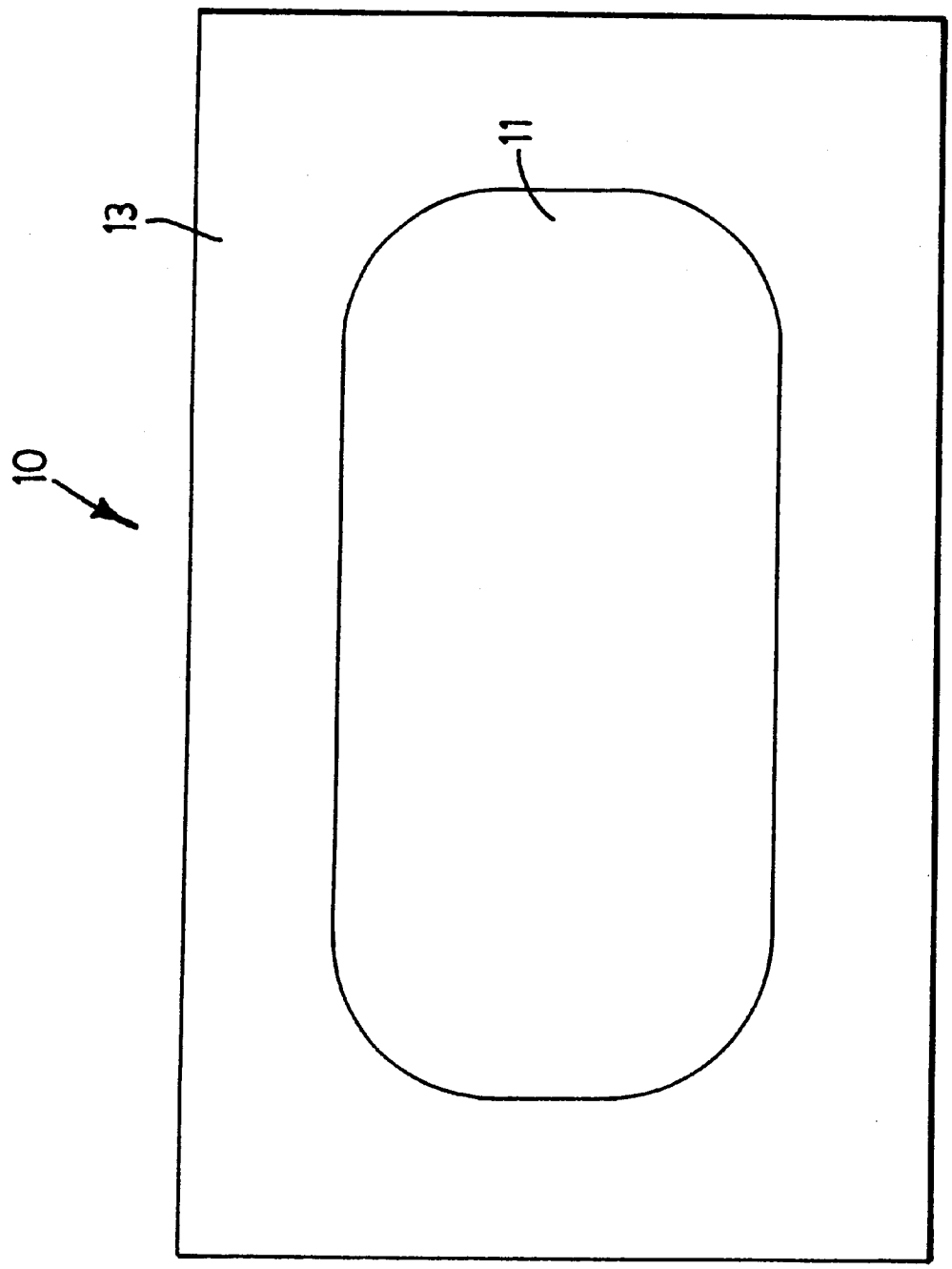
FIG. 1A shows exemplary central and marginal parts of the panel.

FIG. 1 generally illustrates schematically a process and apparatus for hot pressed panel inspection. In the drawing 10A, 10B, 10C represent plywood panels in consecutive positions in their manufacture. Panel 10A is located between the presses of hot press 12. Panel 10B is located for scanning by infra-red scanner 14 and temperature T1 which is substantially the temperature at which the panel emerges from the hot press. Panel 10C is shown in position for scanning by infra-red scanner 16 at temperature T2 below the temperature T1. Each panel 10A, 10B and 10C comprises a central part 11 (see FIG. 1A) and a marginal part 13 extending around it.

The scanned data from scanner 14 is digitized in digitizer 18 and the scanned data from scanner 16 is digitized in digitizer 20. Data from digitizer 18 together with data from thermodynamic sensors 22 to compute the thermodynamic model in computer 24. Similarly data digitizer 20 together with data from sensors 26 are used to compute a second thermodynamic model by computer 24. Computer 24 then compares the thermodynamic model to calculate significant variation in anisotropies.

Large In-Situ Panel Inspection

Another example of the process of the invention is use for in-situ inspection of large panels, for example, metal panels.

In this case, although the problem is different, the principle is the same.

Large in-situ panels, iron or steel panels, must from time to time be inspected for corrosion. These panels might form part of the exterior hull of a ship above the water line, the exterior of a large storage tank or vessel, or in general the panel sheathing of some large structure already in place.

In this case the apparatus may comprise:

1. The single Far IR scanner capable of imaging the panel surface with the required resolution.
2. A digitization and storage unit that buffers the images taken.
3. Means to heat the panel such as a hose to produce a steam or hot water or hot fluid and direct it at the panel surface to induce significant local heating. The hose may be used to heat the panel just prior to the acquisition of the first image. Alternately if the panel has been heated by the sun, it may be sufficient to induce a thermal transient merely by pumping cool water against the hot surface. The second image may be taken after a suitable amount of time has passed. For empty tanks or ship's holds 20–40 minutes might be a suitable amount of time. For vessels or holds filled with dense liquids, a considerable shorter time would be appropriate.
4. An image processing computer system capable of performing the thermodynamic modelling calculations on the set of first images and computing the differences between these time forward modelled first temperature distributions, and actual second temperature distribution sampled.

5. Image processing hardware and software capable of enhancing, identifying and quantifying the detected variations between the later image sample, and the time forward modelled data from the earlier images.
6. An output printing device capable of printing pseudo colour images, or contour map displays reproducing the Far IR images with areas of non uniformity enhanced, and marked.

A first image is scanned at a first temperature and a second image is scanned at a second different temperature after the induction of a sudden thermal transient. The images are digitized.

In this case panel temperature are high (50 to 70 degrees Celsius above ambient), a single Far IR scanner is used, and detailed knowledge of internal construction (nature of internal support and structure) is necessary.

Spatial resolutions of on the order of ¼" square are required, and image processing systems must store and process 400×200 pixels/image for 8'×4' panels, and up to 1200×600 pixels/image for 24'×12' panels.

Adequate image and mathematical processing must be provided (up to several billion operations per seconds).

Ideally an automatic azimuth and elevation control device for directing the Far IR imaging system will be used, and a large portion of the structure scanned using a long focal length imaging system, before the second set of identically located images is taken for differential comparison against the thermodynamically time forward modelled images from the first imaging pass.

Similar considerations concerning central and marginal parts may be applied to these panels. Marginal heat/cooling effects may be, on the one hand, greater than those in FIG. 1 because the panel is metal, but, on the other hand, each panel may be bounded by other panels thus mitigating cooling irregularities. The final choice of the size and shape of the central part may be somewhat similar to that of FIG. 1.

Figure 2:
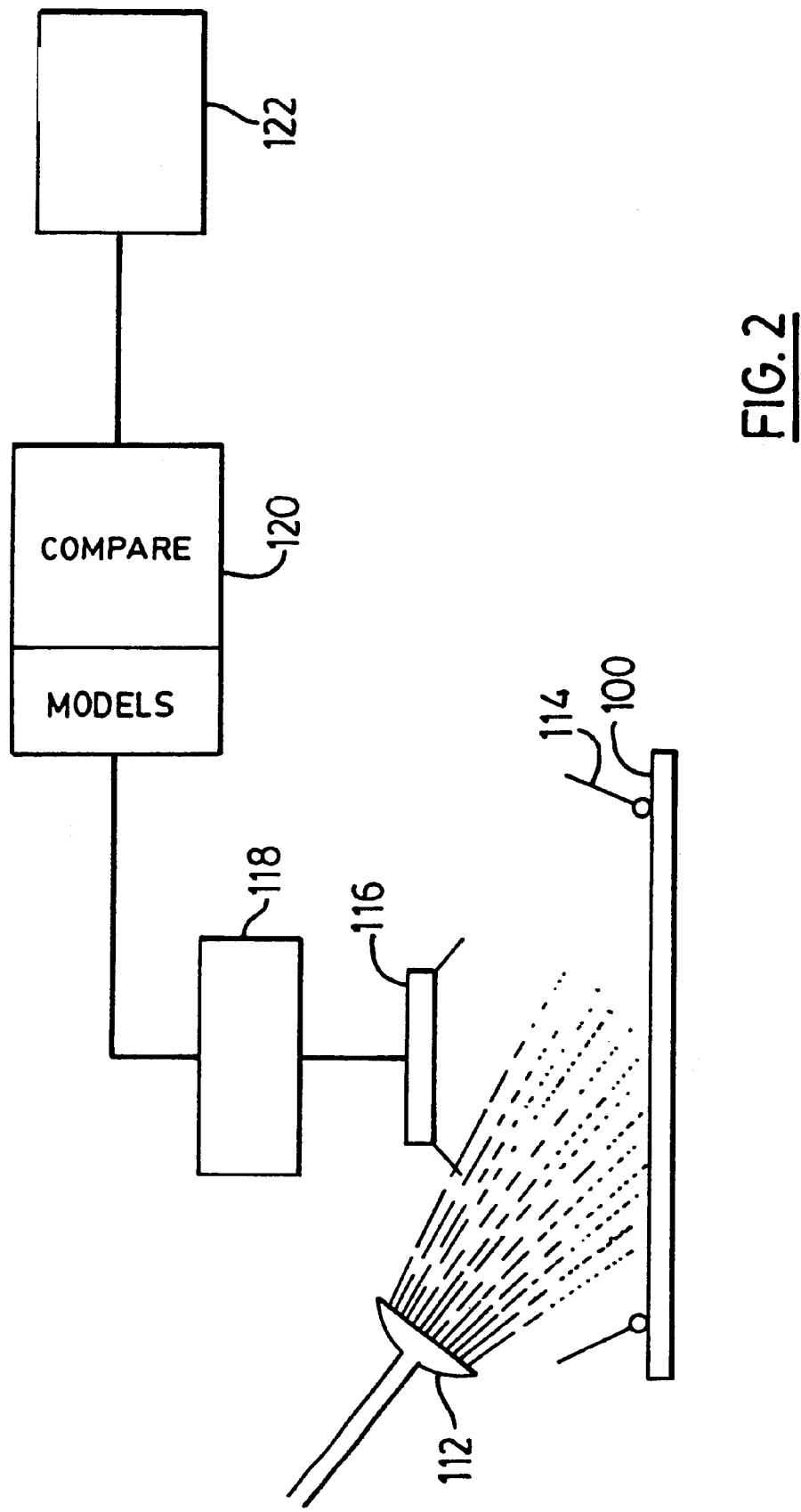
FIG. 2 is another schematic representation of one embodiment of the invention.

FIG. 2 generally illustrates schematically apparatus and process for inspection of a large in-situ panel.

A panel 100 is heated (or cooled) by any suitable means 110. The means 110 may suitably be a hose to deliver hot (or cold) water at a constant temperature. The water is delivered to a top surface of the panel 100 over a period sufficiently to provide relatively uniform surface temperature changes in the panel to bring it to a temperature T10. Temperature T10 may be measured by heat sensors 114 distributed over the surface of the panel.

At temperature T10 infra-red scanner 116 forms an image of the top surface of the panel. The image is digitized in digitizer 118. The digitized image together with information from the sensors 114 is fed to computer 120 where a thermodynamic model of the surface of panel 100 at temperature T10 is made.

The panel 100 is then allowed to change temperature to temperature T12. A second image is scanned by infra-red scanner 116, digitized in digitizer 118 and fed to computer 120. A second thermodynamic model is formed. The two thermodynamic models are compared in the computer to calculate significant variations in anisotropies between the images. The computer may conveniently be provided with a printer 122 for providing this information to the operator.

In-situ Inspection of Pipe

The invention may also be used to inspect pipe. The detailed inspection of buried pipelines, semi buried pipelines, surface pipelines as well as other in-service pipelines conventionally presents problems.

In the case of pipelines transporting a liquid product, ultrasonic measures of exterior wall thickness are possible using internal pigging. This process is not so easy for pipelines transporting certain products, or for certain thick-walled pipelines transporting corrosive or abrasive slurries.

In the case of gas pipelines, a pipeline might first be pigged with some sort of magnetic, dimensional or ultrasonic detector, and anomalous sections exposed for further examination.

In the case of pipelines carrying corrosive, or abrasive slurries, or other materials difficult to pig, the pipes may already be exposed.

In either case the application of the invention in this case is the detection of external surface corrosion internal surface corrosion, or wall thinning, in the pipe. Apparatus used is:
1. An induction, or other heater (providing 500–10,000 watts of heat) is mounted on an external rolling frame which moves in a controlled linear (or spiral) fashion over the surface of the pipe, or alternately which can move beside the pipe as in a truck mounted system, or alternately a cooling system either frame or truck mounted for spraying cold water, if the pipe is already warm.
2. A first and second IR scanner are also mounted on this external tracking unit, or alternately if transient bursts of heat are employed a single scanner used to capture the high speed progression of the transient.
3. A digitization and storage unit that buffers and sequences the images taken is connected to allow the flow of data from the Far IR scanners.
4. Sufficient tachometers, orientation measurement devices, and local ambient thermometers are provided to allow for accurate and efficient tracking of the external scanning frame or truck, and to allow accurate thermodynamic modelling of the associated heat loss in scanning, or alternately a second imaging system which acquires normal visible images of the affected pipe, which allows for later direct identification of the detected defects on the visual image.
5. An image processing computer system capable of performing the thermodynamic modelling calculations on the set of first images and computing the differences between these time forward modelled first temperature distributions, and the actual second temperature distribution sampled, or alternately a high speed processing system which is capable of discriminating the presence of small anomalies in IR images as they are compared to "good" IR images.
6. Image processing hardware and software capable of enhancing, identifying and quantifying the detected variations between the actual second image sample, and the time forward modelled data from the first image.
7. An output printing device capable of printing out pseudo colour images, or contour map displays reporting the Far IR images with areas of non uniformity enhanced, and marked.

A temperature transient is induced in the pipe, either heating, for example by using a heater or surface steaming, or by cooling, for example by using cold water. Images are acquired throughout the application of the transient change, and these images are digitized.

In this case pipe surface temperatures are moderate (20 to 80 degrees Celsius above ambient), heat transfer is extremely rapid (depending upon the nature of the pipe contents being transported), and temperature differences are smaller. In a preferred embodiment, the IR scanner or scanners acquire(s) a large number of detailed images to completely document the transient.

Spatial resolutions of on the order of 0.5 mm square or better may be required. Image processing systems must store and process very large amount of data (600×600 pixels or more for a 30 cm square patch of pipe surface).

Adequate image and mathematical processing must be provided (up to several tens of billion operations per second) to perform image processing and thermodynamic modelling at rates adequate to keep up with the inspection of the pipe. Alternatively, mass storage devices may be employed to buffer "snap-shot" data, and computing may be performed in burst mode. In this case no central part and marginal part may be designated.

Figure 3:
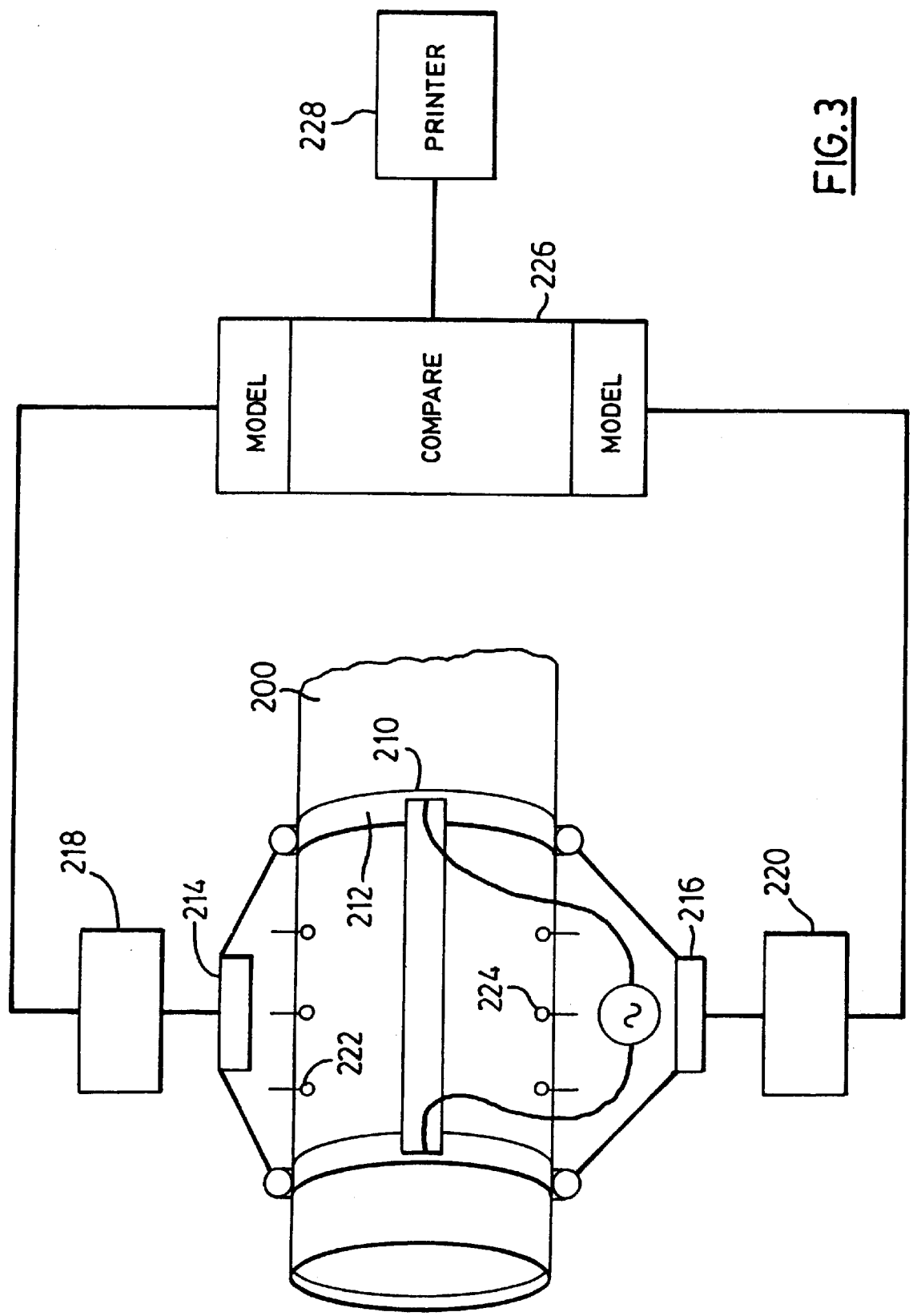
FIG. 3 is yet another schematic representation of one embodiment of the invention.

A process and apparatus for in-situ inspection of pipe is generally illustrated schematically in FIG. 3. An indication heater 210 is mounted on a pipe 200 on a external rolling frame 212. First and second IR scanners 214, 216 are also mounted on the external frame.

The pipe is heated as the induction heater moves over the surface of the pipe and the surface of the pipe is scanned by scanner 214 at temperature T20 and by infra-red scanner 216 at temperature T22 which is lower than temperature T20. The scanned images from each of infra-red scanners 212, 216 are digitized respectively in digitizers 218, 220.

The digitized images from the digitizers are fed with respective temperative information from sensors 222, 224 to computer 226. The computer first forms respective thermodynamic models of the images and then compares them to note any significant variations and an isotropies. These may be indicated to the operator by means of a printer 228.

Figure 4:
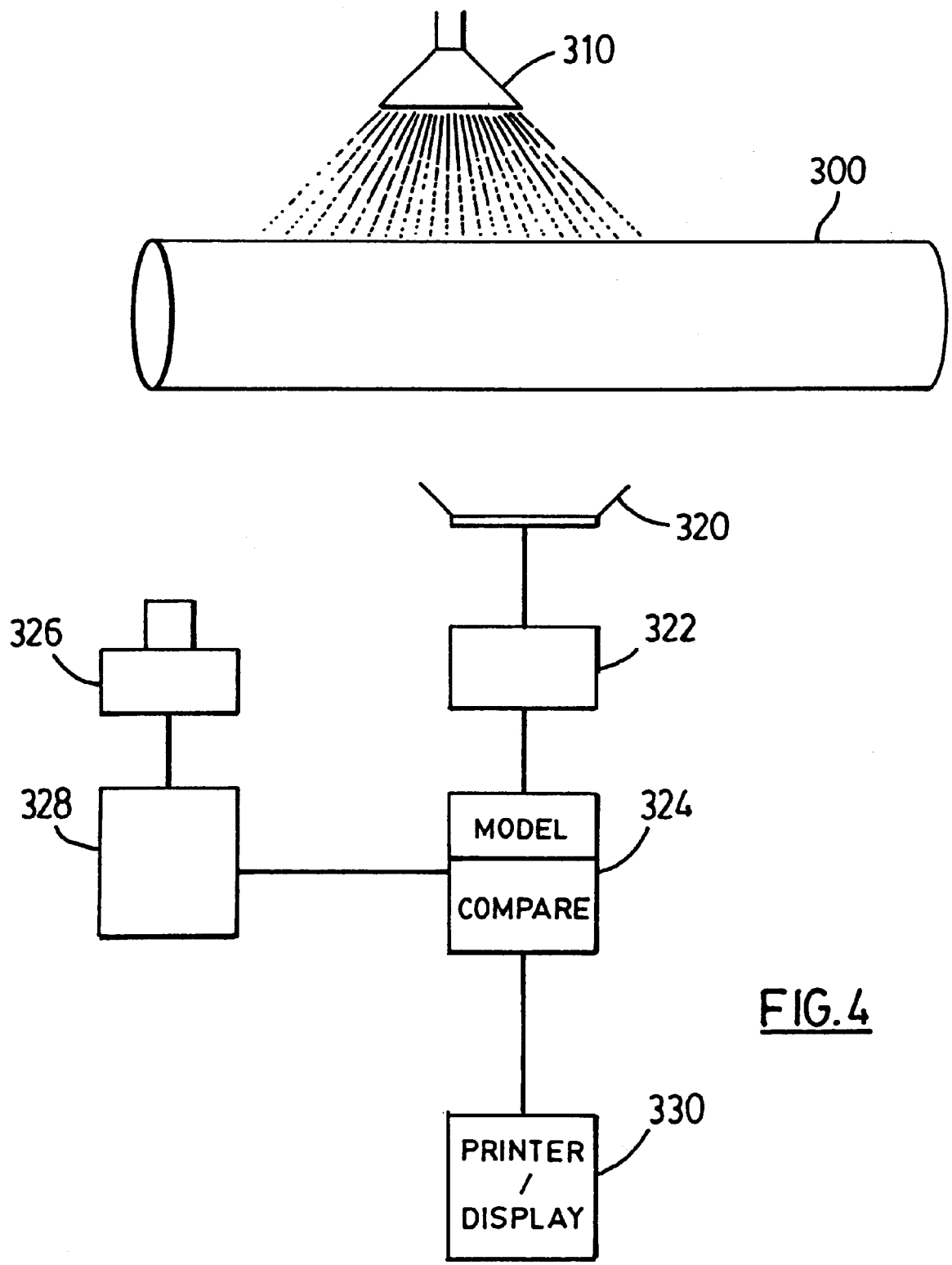
FIG. 4 is yet another schematic representation of one embodiment of the invention.

FIG. 4 illustrates another process and apparatus for in situ pipe inspection for use on a pipe which is already hot, perhaps because it is carrying heated contents. Cooling means, for example a nozzle 310 for cold liquid such as water, is directed towards a pipe 300. The nozzle 310, which may be a spray nozzle, a jet nozzle, a hose outlet or specialist nozzle to produce a set liquid pattern, may be mounted on an external transport means (not shown) of any convenient type. An IR scanner 320, is provided in the region of the pipe portion to be cooled by liquid from the nozzle 310. The scanner 320 may be mounted on the same transport as the nozzle.

The pipe 300 is cooled by liquid spray from the nozzle 310 and the surface of the pipe 300 is scanned by scanner 320. The scanned images from the infra-red scanner 320 are digitized by digitizer 322.

The digitized images from the digitizer 322 are fed with respective temperature information from sensors 327, via digitizer 328 to computer 324. The computer stores the transient heat changes observed, notes and calculates models and highlights anomalies on a separate scanned image taken by an ordinary video camera 326 digitized by digitiser 328.

These highlighted anomalies can then be directly identified with normal image data and presented on any display or on printer 330.

Figure 5:
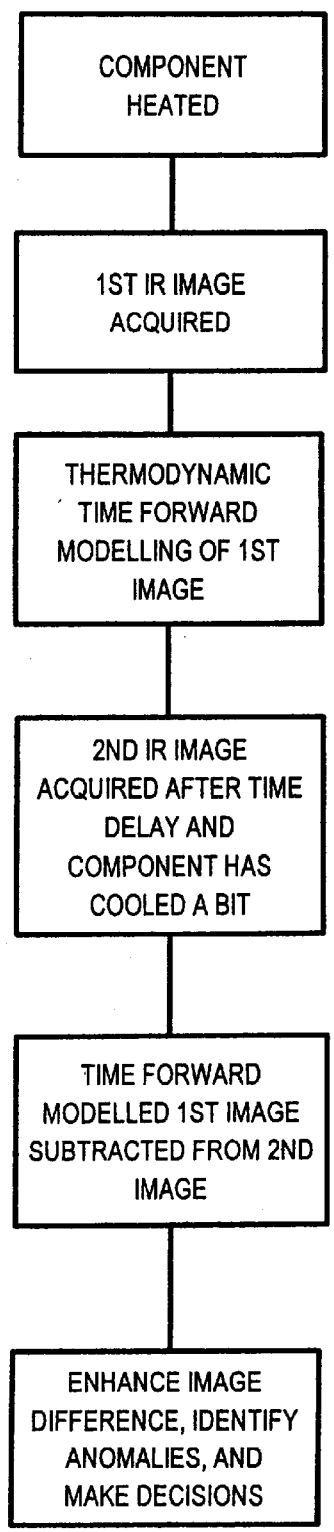
FIG. 5 is a flow chart.

FIG. 5 is a simplified flow chart defect detection by computer modelled dissipation correction time delayed Far IR scanning.

FIGS. 6, 7, 8 and 9 show experimental results.

The invention will now be further described with referencing to the following example.

EXAMPLE

Experiment

There were three stages in the experiment. The first stage was a preliminary test using an oven to heat panels and image panels. In the second stage efforts were made to fabricate panels with "known" density patterns and image the hot panels after they came out of the press. A Far infra-red (3–10 microns wavelength of peak sensitivity) imaging system was installed to image the panels. Destructive measurement for comparison was the third stage. Some of the results are illustrated in FIGS. 6, 7, 8 and 9.

Oven Test

An oven size 5'×5'×5' was used to heat 4'×4' OSB panels to different temperature levels. Panels of relatively uniform density had patterns of thickness variation cut into their surfaces. These panels were then heated in the oven until they reached an equilibrium temperature, then were removed from the oven and allowed to cool. A sequence of Far IR images of the panels were taken as they cooled, and the data digitized with 12 bits of resolution in images approximately 400 pixels per square inch. The distances between the camera and panels were from 1.5 to 4 meters.

This procedure quickly showed that an effect was present, but only if the variations in the panel thickness were of significant size (approximately 1 to 2 inches in diameter, and 20% in thickness of greater). It also showed that the panels showed the most obviously identifiable effect after a period of 6 to 8 minutes (for panels of approximately ⅜" thickness starting at temperature of 80–100° C. and cooling to room temperature).

In addition to the cooling-down process, images were also taken during the heating-up process. Panels started at room temperature (approximately 20° C.) were placed in front of the open oven doors, and heat impulse from the oven allowed to propagate through the internal structure of the panels. This approach resulted in clearer images if the oven-panel-camera system could be set up properly to allow for a uniform heat up of the panel.

Panel Fabrication

The raw wood material used was Aspen strands. Two 4'×8'×7/16" OSB panels with a target density 640 kg m$^{-3}$ were manufactured using an automatic forming line and press system. The platen temperature was about 405° F. (207° C.). After the panel exited the press, it was laid horizontally on insulating cardboard on the floor just past the press area. The panel was continuously monitored for about 15–20 minutes using the Far IR camera which was installed approximately 5 meters above the floor looking down at about 60 degrees. Images were taken every 45–60 l seconds.

Low and high density anomalies were attempted in the fabrication. In the first panel, larger structural defects were created at the core layer. Low density holes (4 to 5 inches in diameter) and strips (approximately 4 inches width, 24 inch length) were clearly detected by the IR imaging system.

In the second, smaller scale density variation spots were created. When strands were deposited to ⅔ of the total mass of the mat. 8 columns of high and low density spots were made. Each column had 4 spots of different sizes from 1 inch to 4 inches in diameter. Spots were 1-foot apart in both panel length and panel width directions. A certain percentage of strands from one column of spots were taken and added to the column next to it, thus creating alternated high and low density spots. The percent of strands taken and added were intended to vary from approximately 10 to 40% by weight. Caution was taken to minimize disturbance to the rest of the mat. Although attempts were made to create both high and low density spots, only low density spots were successfully created. Neither IR images nor destructive measurement clearly showed the high density spots as expected. This is probably because, when depositing the other ⅓ of the strands, a large portion of strands fell on top of the high spots got scattered.

In order to qualitatively retrieve the density distribution of the second panel, a very simple modelling has been applied to the temperature image. In the model it has been assumed that the primary heat loss is through the upper surface of the panel conducting heat into the air. Heat loss from the edges has only crudely been estimated.

Destructive Measurement

The second fabricated 4'×8' panel was cut into 50×50 mm (close to 2"×2") specimens. Length, width, thickness and weight were measured to calculate density for each specimen. The actual sizes and densities of the low density spots on the fabricated panel were also obtained from this destructive measurement. The actual densities of these spots varied from 430 to 590 kg m$^{-3}$, approximately 37 to 92% lower than the average panel density. The sizes of these spots varied from about 1 to 6 inches.

Results and Discussion

Figure 6:
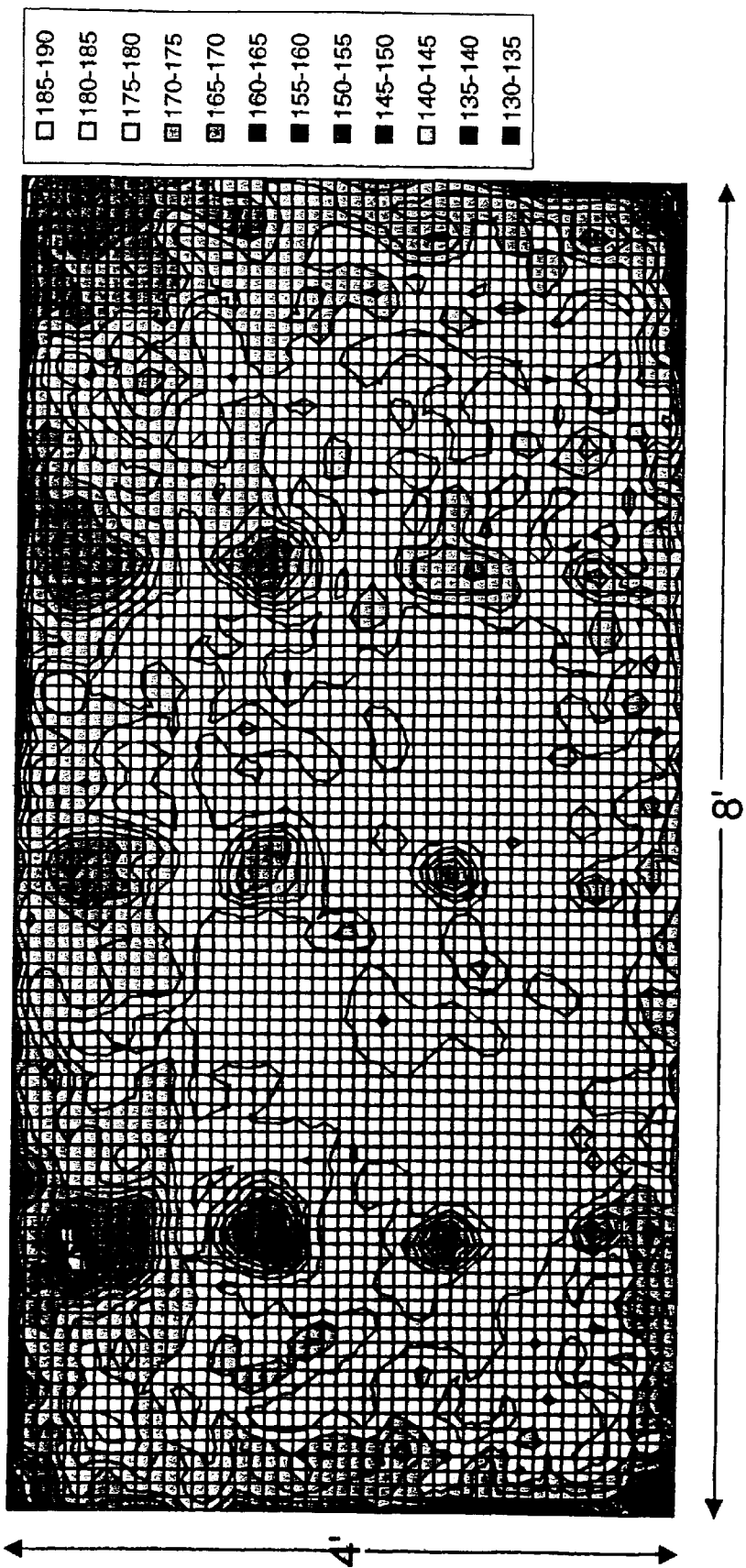
FIGS. 6, 7, 8 and 9 show experimental results utilising a process according to the invention.

A representation of the temperature variations in the second panel is shown in IR image (FIG. 6). The panel reached these temperatures about 5 minutes after it came out of the press. Comparing this temperature distribution with the density distribution from the destructive measurement (FIG. 7), it is immediately evident that the IR image system picked up most of the fabricated low density spots very well. The sizes and locations of these spots are clearly indicated by low temperature areas on the IR temperature map. Although there was some edge effect (Panel cools down fast on its edges, because of the fast heat loss). The four smallest low density spots located at the lower part of the panel, which have densities about 13 to 33% below the panel average with sizes varying about 1 inch to 2 inches, can be seen from the IR temperature map (FIG. 6).

It was observed that good images could be obtained in a fairly large temperature range (about 50° C. to platen temperature). Reasonably clear images lasted for 10 to 15 minutes on the system's monitor. In other words temperature need not be very specific.

No clear pattern of high density spots as intended showed on the destructively measured density map. This could probably be explained by the mat forming mechanism. If an area on the mat is already higher than its surrounds, the chance that strands falling onto this area stay on top of it is low. They may easily get dispersed. It does not appear to be easy to create high density spots without substantially disturbing the structure of the mat. However, there are some relatively high density areas (720–780 kg m$^{-3}$) on the destructive density map. The high temperature area on the IR temperature map does not correspond well with these high density areas. This is because the thermal range of the IR system was not properly set during imaging, and high temperatures got saturated. This resulted in some loss of resolution in high temperature range.

Figure 7:
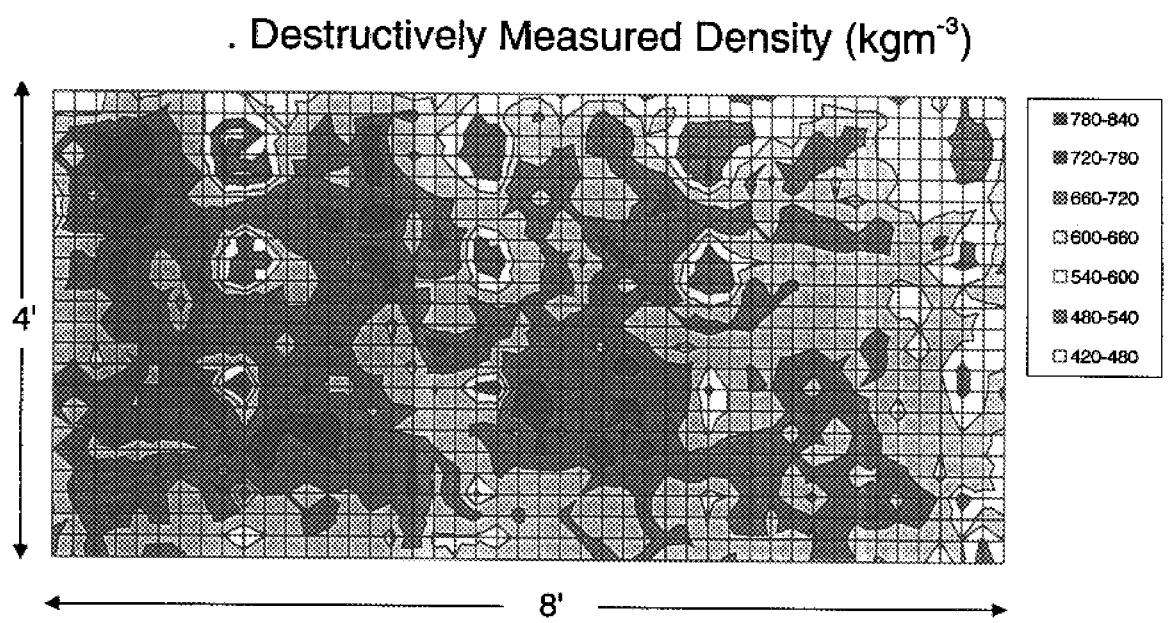
Figure 8:
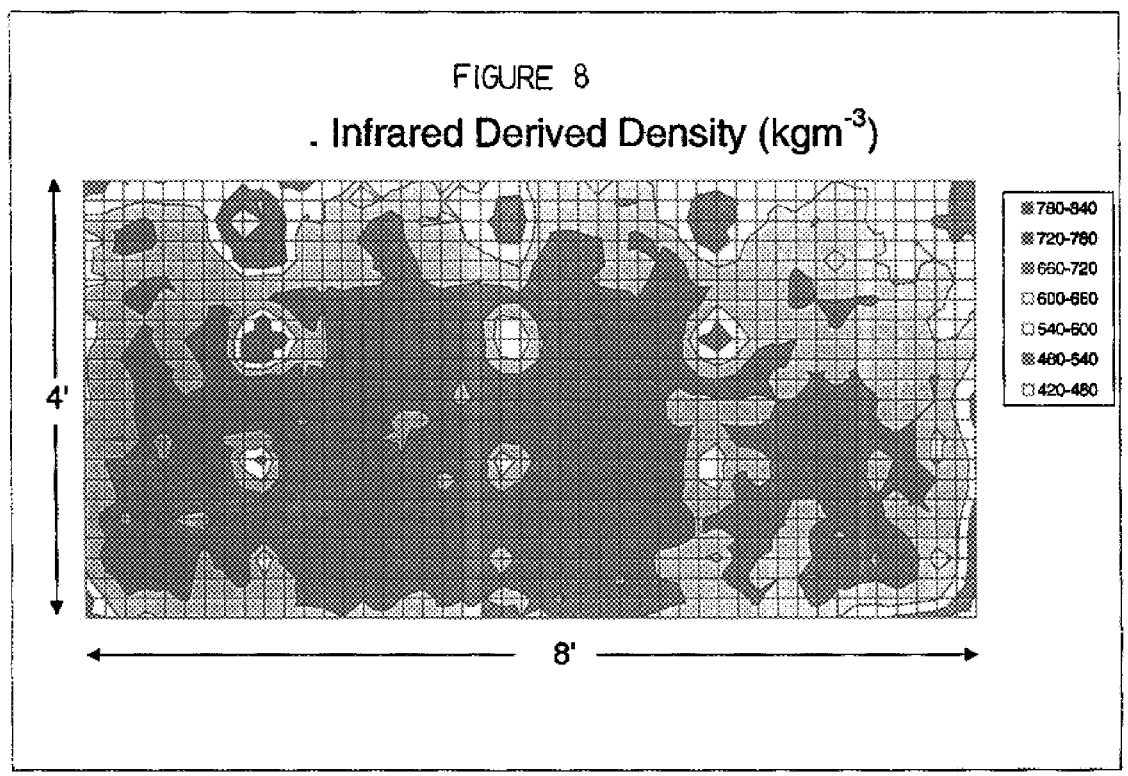
Figure 9:
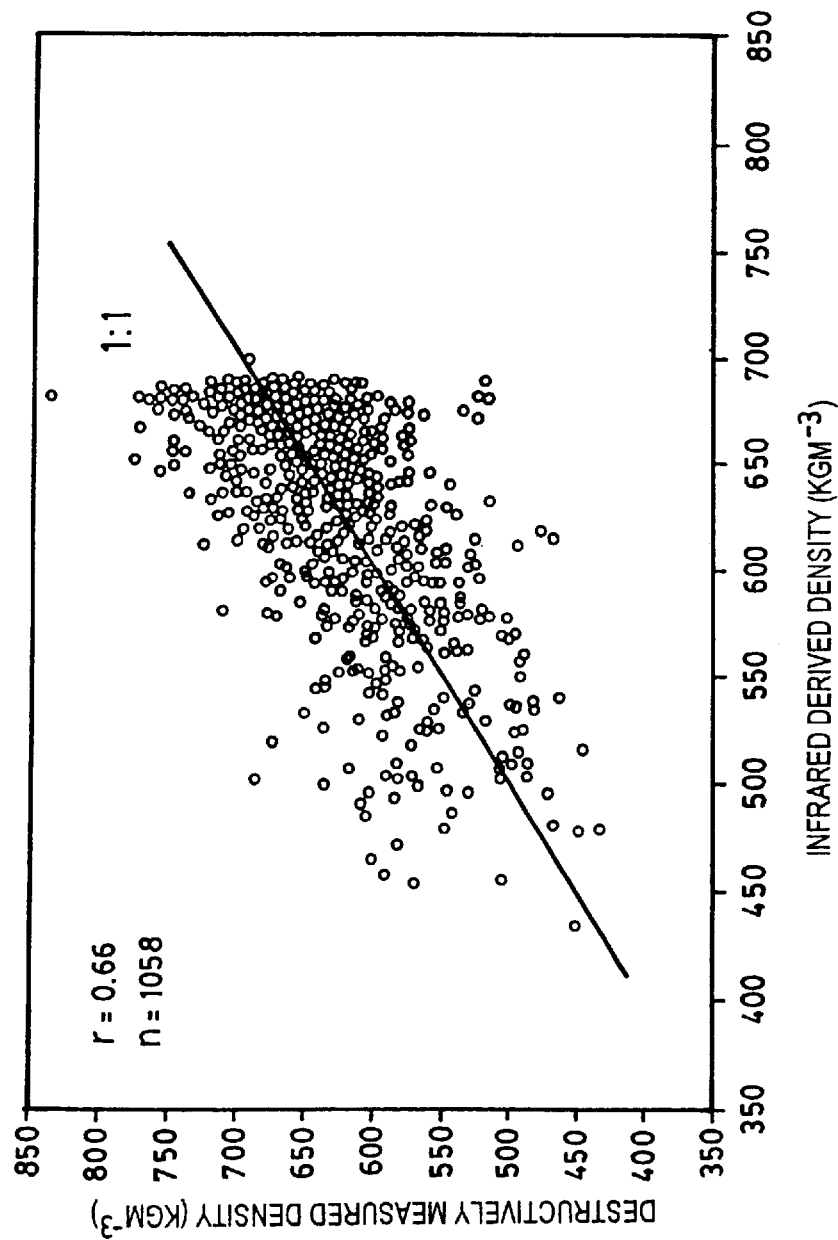

The density derived from IR imaging and simple modelling (FIG. 8) roughly resembles the destructively measured distribution (FIG. 7). The temperature saturation in IR measurement is reflected by a saturation in the derived density at about 690 kg m$^{-3}$ in a chart showing destructive vs. derived densities (FIG. 9). A statistical analysis gave a correlation coefficient 0.66 for the destructive and the derived density.

A computer simulation study of OSB panel horizontal density variation conducted at the Forintek Canada Corp. indicated that even under relatively optimal mat forming conditions the horizontal panel density could deviate up to 16% and 30% from its average for a specimen size 2-inch square and 1-inch square respectively. With the capability of detecting about 13% density deviation at about 1 inch spatial resolution, IR could be practically useful for estimate of OSB panel horizontal density distribution.

Conclusions

This study shows that the infra-red imaging technique is capable of detecting OSB panel horizontal density. Anomalies of a scale greater than 1 inch in diameter and of a deviation in density of about 10–15% below the panel average is surely measurable. 10–15% above the average should also be detectable. In other words, a 10–15% density deviation from the panel average should be detectable.

The detectable temperature range is large (about 50° C. to platen temperature), this means that panels need not be imaged immediately after their exit from the press. The time required for imaging and processing images depends on the camera, computer and software used. Speed should not be a problem for on-line measurement.

Overall, this technique may be suitable for inspecting OSB panel density/variability.

I claim:

1. A process for the detection of flaws in an article using Far infra-red scanning of its surface comprising changing the temperature of the surface of an article over a plurality of temperatures and making an infra-red scan at each of said temperatures during changing the temperature, the infra-red scans being separated one from another by equal time increments;
   characterized in the steps of allocating parts of said surface as central and marginal parts, forming images from said infra-red scans, digitizing said infra-red scans, digitizing the images to provide a sequence of digitized scanned images;
   for said central part of the surface, comparing data directly from said digitized scanned images and noting variations and/or anisotropies from a general cooling pattern for the article and deducing the presence of flaws at locations in the article corresponding to the location of the variations and/or anisotropies in the comparison of the digitized scanned images; and
   for the marginal part of the surface, performing thermodynamic modelling on one of the digitized scanned images to provide an estimate of the temperature distribution for a hypothetic unflawed article after passage of one of said time increments, and comparing data from an adjacent digitized scanned image with said estimate and noting variations and/or anistropies of the structure of the marginal part of the article.

2. A process as claimed in claim 1 in which 10 to 90% of the surface of the article is allocated as the central part.

3. A process as claimed in claim 2 in which the marginal part has regularity about the central part.

4. A process as claimed in claim 2 in which from 20 to 80% of the surface is designated as central part.

5. A process as claimed in claim 4 in which about 75% of the surface is designated as central part.

6. A process for detection of flaws in an article comprising changing the temperature of the surface of an article over a plurality of temperatures; making an infra-red scan at each of said temperatures during changing of temperature; said infra-red scans providing at least a first and a second scanned image and being separated one from the other by a time increment; digitizing the at least first and second scanned images to provide a sequence of at least a first and a second digitized scanned image; performing thermodynamic modelling on the first digitized scanned image to provide an estimate of the temperature distribution for a hypothetic unflawed finite article after passage of said time increment; comparing data from said second digitized image with said estimate, noting variations and/or anisotropies of the structure of the article.

7. A process for detecting flaws in the structure of an article, said process comprising the steps of:
   producing a change in temperature of the surface of the article;

making an infrared scan of the article at a measured time interval after said change in temperature, and said infrared scan comprising an image;

digitizing said infrared scan image to generate a digitized image and obtaining temperature distribution data from said digitized image;

performing thermodynamic modelling of a hypothetic finite article to provide an estimate of temperature distribution in said hypothetic finite article after said measured time interval;

comparing said temperature distribution data with said estimate of temperature distribution for said hypothetic finite article for noting variations for the structure of the article.

* * * * *